United States Patent [19]
Shaw et al.

[11] 4,017,373
[45] Apr. 12, 1977

[54] ELECTROCHEMICAL SENSING CELL

[75] Inventors: Manuel Shaw, Bel Air; Imbrie Thatcher, Chatsworth, both of Calif.

[73] Assignee: Interscan Corporation, Chatsworth, Calif.

[22] Filed: Apr. 5, 1976

[21] Appl. No.: 673,963

[52] U.S. Cl. .......................................... 204/195 R
[51] Int. Cl.² ...................................... G01N 27/46
[58] Field of Search ............ 204/195 R, 195 P, 1 T, 204/1 P, 1 N, 1 F

[56] References Cited

UNITED STATES PATENTS

| | | | |
|---|---|---|---|
| 3,886,058 | 5/1975 | Barna | 204/195 P |
| 3,966,579 | 6/1976 | Chang et al. | 204/195 R |

*Primary Examiner*—G. L. Kaplan
*Attorney, Agent, or Firm*—Howard A. Silber

[57] ABSTRACT

An electrochemical sensing cell includes a planar sensing electrode clamped between a manifold cap and a cover for a container housing the counterelectrode and electrolyte. In the manifold cap, the gas being analyzed flows through a shallow recess into contact with one side of the sensing electrode. The cover includes an opening across which is supported a porous disc saturated with electrolyte. When the cap is secured to the cover, the disc presses against the other side of the sensing electrode to ensure good electrolyte contact therewith. A vent hole in the cover also permits replenishing of the electrolyte without major disassembly of the cell.

12 Claims, 3 Drawing Figures

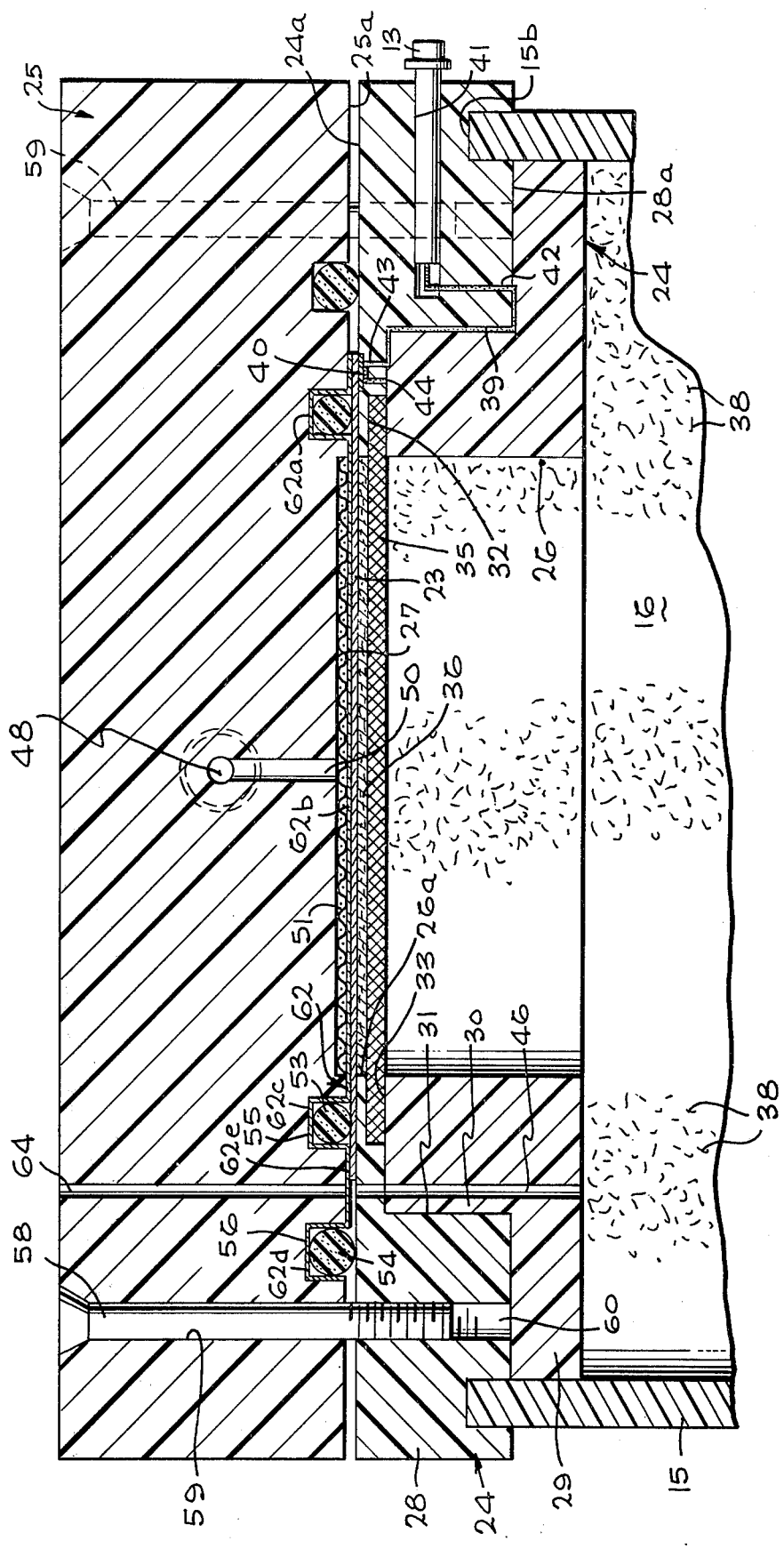

ELECTROCHEMICAL SENSING CELL

BACKGROUND OF THE INVENTION

1. Field of the Invention

The present invention relates to an electrochemical sensing cell, and particularly to an improved housing for such a cell.

2. Description of the Prior Art

Concern for the quality of the air we breathe has led to mandatory requirements for monitoring of air contaminants. Federal and state environmental protection agencies have imposed such monitoring requirements both to ensure compliance with statutes establishing maximum pollutant levels, and to provide a data base for evaluation of the contamination problems associated with certain industries, power generation plants, motor vehicle exhausts and other pollutant sources. To accomplish such monitoring, the need exists for simple, inexpensive, accurate and trouble-free monitors, and it is a principle object of the present invention to provide an improved electrochemical sensing cell useful in such an instrument.

An electrochemical sensing cell is a device which generates an electrical current only in the presence of the pollutant being measured. The magnitude of this current is proportional to the pollutant concentration, which may be indicated by a meter connected to the output of an amplifier which amplifies the current from the sensing cell.

An electrochemical sensing cell incorporates two electrodes, one called a sensing electrode and the other called a counterelectrode, immersed in an electrolyte. When the pollutant gas contacts the sensing electrode, reactions occur which cause a current to flow in a circuit comprising a counterelectrode, the electrolyte, the sensing electrode and an external lead connecting the sensing electrode back to the counterelectrode. The magnitude of this current is proportional to the pollutant concentration. By the appropriate selection of counterelectrode and electrolyte materials, in conjunction with external biasing, the sensing cell may be made selective to a particular gas species. For example, the sensing cells disclosed in the Chand/Shaw U.S. Pat. Nos. 3,622,487 and 3,622,488 are intended selectively to detect nitrogen oxide and sulfur dioxide respectively.

The basic electrochemistry of such sensing cells is well known. Depending on the species to be detected, either oxidation or reduction occurs at the sensing electrode, and the complementary reaction occurs at the counterelectrode. For example, to detect hydrogen sulfide ($H_2S$), oxidation occurs at the sensing electrode, which preferably comprises a noble metal such as gold or platinum. Electrochemical reduction occurs at the counterelectrode, which may comprise lead in an electrolyte of sulfuric acid. Preferably, the counterelectrode is non-polarizable, so that it does not change its potential when current is passed through it. This permits the counterelectrode also to function as a reference electrode. That is, the reduction potential associated with the reduction reaction at the counterelectrode is a fixed potential against which the oxidation potential at the sensing electrode may be referenced. Since these potentials are known per se, an appropriate bias voltage may be selected to ensure that only $H_2S$ gas is oxidized at the sensing electrode. The oxidation/reduction potentials are set forth in standard chemical texts such as that by Wendell Latimer, entitled OXIDATION-REDUCTION POTENTIALS.

There are many practical problems associated with packaging electrochemical sensing cells. Certain of these concern the sensing electrode. Cell operation requires that the sensing electrode be in contact with the electrolyte so that the requisite oxidation or reduction can occur at the sensing electrode with appropriate current flow through the electrolyte. At the same time, the sensing electrode must be exposed to the gas being analyzed. That is, molecules of the gas species being detected must be able to reach the sensing electrode where they are oxidized or reduced. These two requirements of (a) contact with the electrolyte and (b) exposure to the gas being sensed place conflicting demands on the sensing electrode. If the area of exposure to the gas is large, the opportunity exists for excessive evaporation of the electrolyte. Furthermore, leakage of the electrolyte through the sensing electrode also may be a problem. One approach of the prior art, utilized in the above mentioned Chand/Shaw patents and in the U.S. Pat. Nos. 3,429,796 to Lauer and 3,755,125 to Shaw, involves the use of a thin membrane covering the sensing electrode. The membrane provides a liquid tight seal that prevents leakage and reduces evaporation of the electrolyte. The membrane material is porous to the gas being sensed, which passes through the membrane to the sensing electrode.

Another requirement of the sensing electrode is that it have a large effective surface area. In the above cited Chand/Shaw and Lauer patents, this was accomplished by using a micromesh screen of gold or platinum as the sensing electrode. An alternative approach utilizes fine particles of the noble metal bound in a polymeric dispersion. This approach is shown e.g., in the German Auslegeschrift No. 1,233,173 to Guthke and Habermann. There, finely powered metals are bound in a porous structure of permutite and a plastic such as polystyrol. The electrolyte diffuses through this porous structure so as to immerse completely the sensing electrode metal particles. The gas being monitored dissolves through the diffused electrolyte to contact the sensing electrode metal. Very good sensitivity is achieved because of the large effective surface area of the powdered metal. Indeed, in some applications it may be desirable to decrease the sensitivity, and this can be accomplished by controlling the amount and density of the permutite in the dispersion.

Electrolyte evaporation also may be a problem in sensing cells of the type which employ separate counter- and reference electrodes. For example, in one known type of CO monitor, the sensing electrode is located at one end of a cylinder which houses the electrolyte. The reference electrode and counterelectrode are situated at the other end. The counterelectrode requires a supply of oxygen, and this is obtained by exposing the counterelectrode to air. As a result, the evaporation problem described above occurs both at the sensing electrode at one end of the cell and at the counterelectrode at the other end. A much higher evaporation rate results, with concomitantly short sensor lifetime. That is, the electrolyte must be replaced in the cell at relatively short intervals.

Thus, another object of the present invention is to provide an electrochemical sensing cell in which electrolyte evaporation is minimized, so that the cell can be used for long periods of time before the electrolyte must be replenished. Another object of the present invention is to provide such a sensing cell employing a dispersion-type sensing electrode in a housing configuration that minimizes both leakage and evaporation of the electrolyte. A further object is to provide such a cell in which replenishment of the electrolyte, when required, can be accomplished very simply, without major disassembly of the cell.

Another problem associated with electrochemical sensing cells concerns sloshing of the electrolyte. This is undesirable since it may result in intermittent contact between the electrolyte and the sensing electrode. This of course would result in intermittent operation or erroneous measurements. Yet for portability, it is necessary that the cell remain operative despite movement which may occur if the instrument is used in an aircraft, automobile or boat. Another object of the present invention is to provide an electrochemical sensing cell in which the electrolyte is immobilized so as to eliminate the sloshing problem.

Another problem resulting from the structural configuration of the sensing cell concerns the pressurization requirements for the gas being analyzed. Certain cell configurations are such that the gas cannot be pressurized above or below the environmental ambient pressure. Such excess pressure or suction could distort or damage the sensing electrode. With such cells, a sample bag must be employed to collect some of the gas being analyzed and to provide this to the cell at the environmental ambient pressure. A further object of the present invention is to provide an electrochemical sensing cell which can operate with a gas source that is pressurized either above or below the environmental ambient level.

SUMMARY OF THE INVENTION

These and other objectives are achieved by providing an electrochemical sensing cell having a unique housing in which a disperson-type sensing electrode is clamped between a cover for the electrolyte chamber and a manifold cap which provides exposure of the sensing electrode to the gas being analyzed.

In the electrolyte container, an inert absorbent material immobilizes the electrolyte. The cover has a central opening across which is situated a screen that supports one or more porous discs which are saturated by the electrolyte reaching them through the screen. When clamped in place, the sensing electrode presses against these discs so as to ensure good electrolyte contact with no sloshing problem.

The manifold cap includes a shallow recess through which the sample gas flows from a small diameter inlet tube to a small diameter outlet tube. A screen fills the recess to maintain pressure on the sensing electrode and to keep the electrode from touching the bottom of the recess, thereby ensuring intimate sample gas contact with a large area of the sensing electrode surface. Since the sensing electrode is supported over substantially its entire area, it will not distort in shape when subjected to excess or reduced pressures. Therefore, the gas being analyzed may be provided to the cell either under pressure or suction conditions.

A small vent hole through the cover is aligned with a vent hole in the cap that is blocked by a thin porous strip. This arrangement permits venting of vapor from the electrolyte while inhibiting electrolyte leakage. When the cap is removed, the electrolyte may be replenished via the vent hole using a syringe and needle.

BRIEF DESCRIPTION OF THE DRAWINGS

A detailed description of the invention will be made with reference to the accompanying drawings wherein like numerals designate corresponding parts in the several figures.

FIG. 3 is a transverse sectional view of the manifold cap and cover portions of the sensing cell of FIG. 1, as seen along the line 3—3 thereof.

DESCRIPTION OF THE PREFERRED EMBODIMENT

Figures 1, 2:
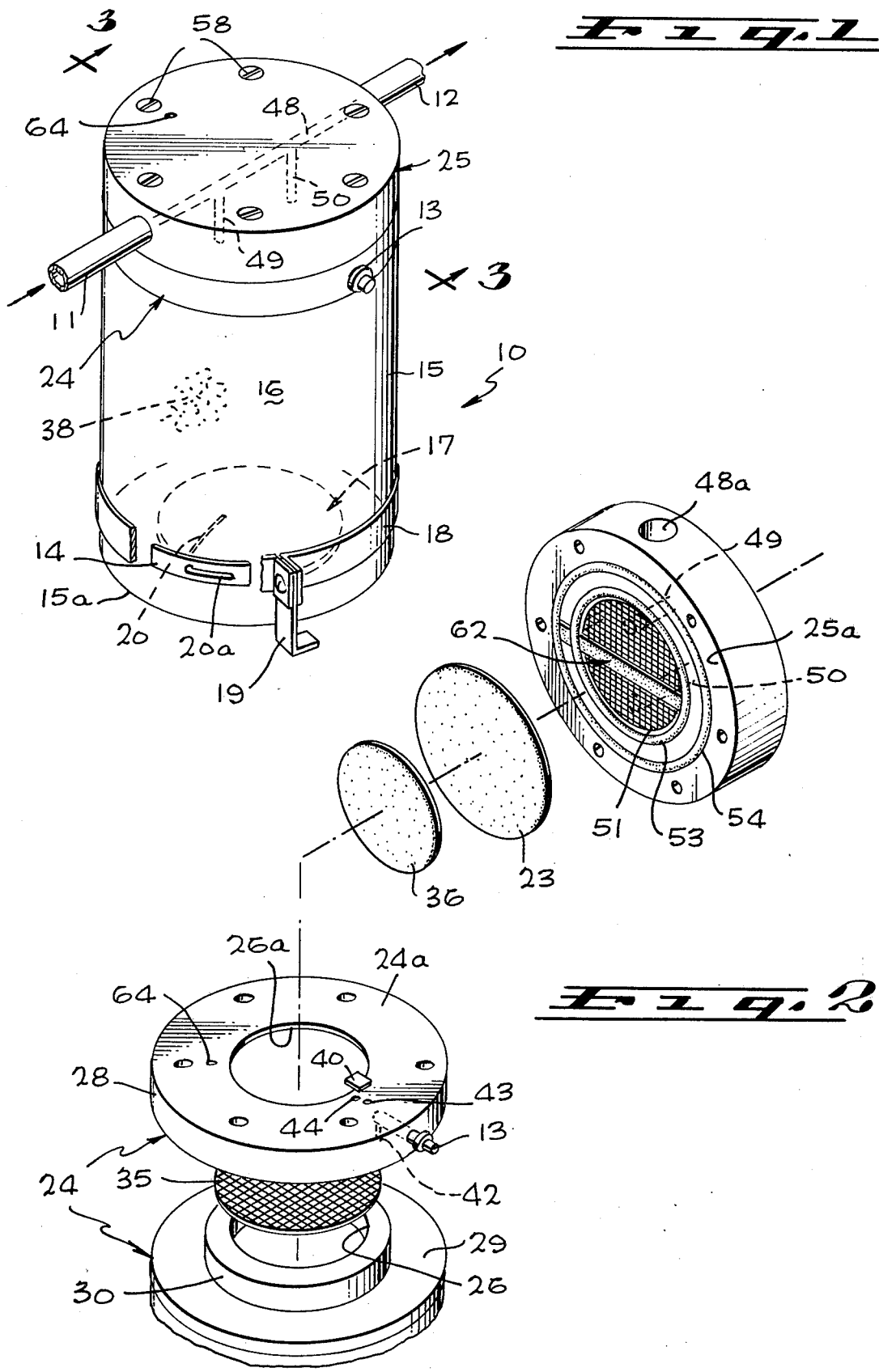
FIG. 1 is a pictorial view of the inventive electrochemical sensing cell, partly broken away to show the manner of electrical connection to the counterelectrode.
FIG. 2 is an exploded pictorial view of the sensing cell of FIG. 1 showing details of the manifold cap and of the cover for the electrolyte container.

The following detailed description is of the best presently contemplated mode of carrying out the invention. This description is not to be taken in a limiting sense, but is made merely for the purpose of illustrating the general principles of the invention since the scope of the invention is best defined by the appended claims.

Referring to the drawings, the inventive electrochemical sensing cell 10 is used to detect and measure the concentration of a particular electroactive gas species in a gas sample. The gas being analyzed flows into the sensing cell 10 via a conduit 11 and exits from the cell via a conduit 12. An appropriate pump (not shown) of either the positive pressure or suction type may be used to force the gas through the sensing cell 10. If the particular species is present, a current will be generated between the sensing electrode terminal 13 and the counterelectrode terminal 14. This current advantageously is amplified and used to drive a meter (not shown) which directly indicates the species concentration, for example, in parts per million. Such amplification and meter circuitry are conventional, and form no part of the present invention.

The sensing cell 10 includes a cylindrical container 15, closed at the bottom 15a, that holds the electrolyte 16 and a counterelectrode 17 immersed in the electrolyte. A metal clamp 18 surrounds the container 15 and serves the double function of mounting the sensing cell 10 to an L-bracket 19 and of providing electrical connection to the counterelectrode terminal 14. That terminal may comprise a thin strip of foil mounted on the outside of the cylinder 15. A wire 20 connected to the counterelectrode 17 extends through a hole in the cylinder 15 and has an end portion 20a that is bent back underneath the terminal strip 14. The clamp 18 covers the strip 14 and insures good electrical contact between the wire 20, the strip 14, and the clamp 18 itself. A wire connection (not shown) is made directly to the clamp 18 or via the bracket 19.

The sensing electrode 23 (FIG. 2) is planar and is clamped between a cover 24 that seats atop the open end 15b of the container 15 and a manifold cap 25 to which the inlet and outlet conduits 11, 12 are connected. The cover 24 has a central opening 26 through which the electrolyte 16 can reach the sensing electrode 23. The lower surface 25a of the cap 25 includes a recess 27 through which the gas to be analyzed reaches the sensing electrode 23. Voltammetric sensing thus is facilitated, since the sensing electrode 23 is in contact with both the cell electrolyte 16 via the opening 26 and the gas species supplied via the recess 27.

As evident in FIGS. 2 and 3, the cover 24 may be assembled from two separate components, a retainer 28 and a plug 29. An annular groove in the bottom 28a of the retainer 28 receives the lip or open end 15b of the container 15, while the plug 29 fits within this container. The retainer 28 has a planar upper surface 24a at the center of which is an opening 26a of the same diameter as the opening 26. The plug 29 also is circular and includes an annular boss 30 which projects upwardly into a bore 31 formed from the underside 28a of the retainer 28. At the "bottom" of the bore 31 is an annular shoulder 32 having a diameter greater than that of the opening 26 but less than the outer diameter of the bore 31. When the boss 30 is inserted as shown in FIG. 3, there is formed an annular ledge 33 which serves to support a disc-shaped screen 35, the periphery of which is clamped beneath the shoulder 32.

The screen 35 supports one or more discs 36 of filter material which function to ensure intimate contact between the electrolyte 16 and the sensing electrode 23. To this end, the screen 35 is formed of a material, typically polyester, that is non-reactive with the electrolyte 16, and which is sufficiently rigid to support the filter disc 36 without becoming concave at its center. The disc 36 has a diameter slightly less than the opening 26a so as to fit within this opening. Typically the disc 36 may comprise a glass filter paper such as that sold commercially. More than one such disc 36 may be required to fill completely the space between the screen 35 and the sensing electrode 23. The electrolyte flows through the screen 35 and completely wets the disc or discs 36. Since these are slightly compressed between the screen 36 and the sensing electrode 23, intimate contact is obtained between the electrolyte that saturates the disc or discs 36 and the sensing electrode 23. To prevent sloshing of the electrolyte 16 within the cell 10, the container 15 may be filled with an inert, absorbent material 38. For example, if the electrolyte is sulfuric acid, this absorbent material 38 may comprise glass-wool.

Electrical connection to the sensing electrode 23 may be made by means of a wire 39 that extends from the terminal jack 13 to a conductive pad 40 situated on the upper surface 24a of the cover 24. As shown in FIGS. 2 and 3, the jack 13 is mounted in a lateral bore 41 in the retainer 28. The wire 39 runs through a hole 42 that extends from the bore 41 to the retainer bottom surface 28a. From there the wire 39 extends along the interface between the retainer 28 and the plug 29, and then extends upwardly through a hole 43 to the surface 24a. The wire 39 then runs along the surface 24a beneath the pad 40 and back into a second hole 44 in the retainer 28. With this arrangement, when the sensing electrode 23 is clamped between the cover 44 and the cap 25, the pad 40 becomes clamped between the electrode 23 and the section of wire 39 that extends along the cover surface 24a between the holes 43 and 44. Good electrical contact results between the sensing electrode 23 and the jack 13. The wire 39 easily can be threaded in place prior to insertion of the boss 30 into the bore 31 (with the screen 35 in place). An adhesive (not shown) then may be used to bond the plug 29 to the retainer 28 so that the cover 24 becomes a unitary element. The one-piece cover 24 then may be bonded directly to the container 15.

After the retainer 28 and plug 29 have been bonded together, a small diameter hole 46 may be bored through the cover 24 parallel to the opening 26. This hole 46 has a double purpose. First, it permits electrolyte 16 to be added to the container 15 by means of a syringe and needle inserted into the hole 46. In this manner, sufficient electrolyte 16 can be inserted to completely fill the cylinder 15 so that the electrolyte remains in contact with the disc 36 regardless of the physical orientation of the cell 10. Secondly, the hole 46 functions as a vent for the electrolyte 15 in the event that the sensing cell 10 is exposed to reduced environmental pressure, as for example when shipped by air.

Only a small portion of the gas being analyzed need be supplied to the sensing electrode 23. To this end, a through passageway 48 is provided in the cap 25 between the inlet conduit 11 and the outlet conduit 12. The ends 48a of the passageway 48 are threaded to accommodate appropriate fittings associated with the conduits 11, 12. A pair of lateral ports 49, 50 branch off from the passageway 48 and extend to the recess 27. These ports 49, 50 are spaced apart so as to be adjacent diagonally opposite edges of the recess 27. In this way, some of the gas entrant through the conduit 11 will flow the branch port 49, into the recess 27 and then out through the port 50 and the outlet conduit 12. Intimate contact between this sample gas and the counterelectrode 23 thus is accomplished within the recess 27. Advantageously, the recess 27 is circular and has the same diameter as the opening 26.

In an alternate embodiment (not shown), a through passageway 48 is not used. Rather, an L-shaped passageway is provided from the inlet conduit 11 to the branch port 49, and a second such L-shaped passageway is provided from the branch port 50 to the outlet conduit 12. With this alternative arrangement, all of the sample gas flows through the recess 27.

Advantageously, a disc-shaped screen 51 is provided within the recess 27. Its purpose is to provide a pressure on the opposite side of the sensing electrode 23 from the discs 36. In this way, when the cap 25 is tightened onto the cover 24, the pressure from the discs 36 will be counteracted by the pressure from the screen 51. Were the screen 51 not used, the discs 36 could distort the sensing electrode 23 into a convex shape in which a portion of the sensing electrode would touch the bottom of the recess 27. Of course, this would reduce the area of the sensing electrode to which the sample gas is exposed, and hence would reduce the sensitivity of the cell 10. The screen 51 typically comprises a polyester or other material that is non-reactive with either the sensing electrode 23 material or the gas being analyzed.

A pair of O-rings 53 and 54 are situated in respective concentric grooves 54 and 55 formed in the lower surface 25a of the cap 25. The diameter of the inner groove 55 and O-ring 53 is slightly greater than the diameter of the opening 26, but less than the diameter of the sensing electrode 23. With this arrangement, when the cap 25 is clamped to the cover 24, the O-ring 53 provides a seal that prevents leakage of the gas being analyzed from the recess 27 past the interface between the cap 25 and the sensing electrode 23.

The cap 25 advantageously is clamped to the cover 24 by means of a set of bolts 58 which extend through counterbored holes 59 in the cap 25 into threaded holes 60 in the retainer 28. When the screws 59 are tightened, the sensing electrode 23 is clamped in place as shown in FIG. 3. The outer O-ring 54 seals the interface between the surfaces 24a and 25a, and thus prevents leakage of the electrolyte 16 along this interface. The diameter of the O-ring 54 is greater than the sensing electrode 23. Advantageously, the hole 46 is situated between the outer periphery of the sensing electrode 23 and the O-ring 54. In this way, the sensing electrode 23 does not block the hole 46, yet any electrolyte 16 that may exit through the hole 46 will be prevented from leaking by the O-ring 54.

During assembly, the screen 51 is held in place by a narrow strip 62 of filter material such as that used for the discs 36. One end 62a of the strip 62 is caught behind the O-ring 53. The mid-portion 62b of the strip 62 diametrically crosses the groove 57 to retain the screen 51 in place. A portion 62c also is caught behind the O-ring 53, and the adjacent end portion 62d is caught behind the outer O-ring 54. The section 62e of the strip 62 between the O-rings 53 and 54 covers the hole 46. Another hole 64 is provided through the cap 25 in alignment with the hole 46. With this arrangement, vapor from the electrolyte 16 will be vented from the cell 10 via the holes 46 and 64. The strip 62 of sintered Teflon or other filter material will prevent the exhaust of liquid through the hole 64.

Advantageously, the sensing electrode 23 comprises a noble metal in particulate form held in a polymeric dispersion of Teflon or other inert material.

Intending to claim all novel, useful and unobvious features, shown or described, the inventors make the following claims:

1. An electrochemical sensing cell of the type having a counterelectrode, a sensing electrode and an electrolyte, and used for detecting a gas species in a fluid sample, said cell comprising:
   a rigid manifold cap having a lower surface, a shallow recess in said lower surface, and spaced inlet and outlet ports communicating to said recess for flowing said fluid sample through said recess,
   said sensing electrode being substantially planar,
   a container housing said counterelectrode and said electrolyte, and
   a cover for said container, said cover having an upper surface on which said planar sensing electrode is situated, said cover having an opening through which electrolyte from said container can contact said sensing electrode, said manifold cap being secured to said cover so that said sensing electrode is clamped between said cap and said cover, so that said fluid sample flowing through said recess is in contact with one side of said sensing electrode over the entire area of said recess, and so that said electrolyte is in contact with the other side of said sensing electrode over the entire area of said opening.

2. A sensing cell according to claim 1 wherein said sensing electrode comprises a metal powder in a polymeric dispersion, and wherein a screen is provided in said recess to prevent said sensing electrode from touching the bottom of said recess.

3. A sensing cell according to claim 2 wherein said cover includes a support screen extending across said opening below the level of said upper surface, and at least one piece of porous material within said opening and compressed between said support screen and said sensing electrode, said electrolyte saturating said porous material and being brought into contact with said sensing electrode via said porous material.

4. A sensing cell according to claim 3 wherein said screen in said recess and said support screen are polyester and wherein said porous material comprises filter paper.

5. A sensing cell according to claim 3 wherein said manifold cap includes a first annular seal surrounding said recess, said sensing electrode being configured so that when clamped between said cap and cover said first seal seats entirely against said sensing electrode so as to prevent the flow of said fluid sample from said recess out of said cell via the interface between said sensing electrode and said cap.

6. A sensing cell according to claim 5 wherein said cover and said cap each has a vent hole, said vent holes being aligned when said cap is secured to said cover, together with a porous strip blocking said vent holes in the interface between said cap and said cover, said strip permitting the venting of vaporized electrolyte but preventing the escape of liquid electrolyte.

7. A sensing cell according to claim 6 wherein said porous strip comprises a filter paper and wherein said strip extends across a screen located in said recess of said manifold cap and is caught under said first seal at both sides of said recess so as to hold said screen in place when said cap is not secured to said cover.

8. A sensing cell according to claim 6 wherein a second annular seal is provided between said cap and said cover, said second seal completely surrounding said sensing electrode, said vent holes being situated between said second seal and said sensing electrode, so that said second seal prevents the leakage from said cell of electrolyte reaching the interface between said cap and said cover either via said opening or via the vent hole in said cover.

9. A sensing cell according to claim 1 wherein said manifold cap includes a channel through which said fluid sample flows, said spaced inlet and outlet ports respectively extending to said recess from spaced locations along said channel.

10. A sensing cell according to claim 1 wherein said cover and said cap both are electrically non-conductive and wherein a connection is provided to said sensing electrode, said connection comprising a wire extending through said cover and projecting along said upper surface, and a pad of electrically conductive material caught between a portion of said sensing electrode and the part of said wire projecting along said upper surface.

11. A sensing cell according to claim 1 together with an inert absorbent material filling said container to immobilize said electrolyte.

12. A sensing cell according to claim 1 wherein said container is held in place by a clamp, and wherein a connection to said counterelectrode comprises a wire extending from said counterelectrode through said container and having a section projecting along the outer surface of said container, and a strip of electrically conductive material caught between said clamp and said projecting section of wire, said clamp being electrically conductive and forming part of the connecting circuit to said counterelectrode.

* * * * *